United States Patent [19]
Yoon et al.

[11] Patent Number: 5,869,060
[45] Date of Patent: Feb. 9, 1999

[54] PORTULACA OLERACEA AND TUMOR CELL GROWTH

[75] Inventors: Ji-Won Yoon; Seung Shi Ham; Hee Sook Jun, all of Calgary, Canada

[73] Assignee: Eastwood Biomedical Research, Inc., Canada

[21] Appl. No.: 759,403

[22] Filed: Dec. 4, 1996

[51] Int. Cl.$^6$ .................................................. A61K 35/78
[52] U.S. Cl. ......................................................... 424/195.1
[58] Field of Search .......................................... 424/195.1

[56] References Cited

FOREIGN PATENT DOCUMENTS 63-208531  8/1988  Japan .

OTHER PUBLICATIONS

Simopoulos et al, Common Purslane: A Source of Omega–3 Fatty Acids and Antioxidants, Journal of the American College of Nutrition, vol. 11, No. 4, 374–382 (1992).

Lau et al, Chinese Medicinal Herbs Inhibit Growth of Murine Renal Cell Carcinoma, Cancer Biotherapy, vol. 9, No. 2, 1994, 153–161.

Verma, et al, Antifertility effects of common edible Portulaca oleracea on the reproductive organs of male albino mice, Indian J. Med Res 75, Feb. 1982, pp. 301–310.

Tulloch, A.P., Leaf Wax of Portulaca Oleracea, National Research Council, Mar. 19, 1974, pp. 664–668.

Huang, Mou–Tuan et al., Inhibition of Skin Tumorigenesis by Rosemary and Its Constituents Carnosol and Ursolic Acid, Cancer Research 54, 701–708, Feb. 1, 1994.

Mohamed, Ali et al, Chemical Composition of Purslane (Portulaca Oleracea), Plant Foods for Human Nutrition, vol. 45, 1–9, 1994.

Retsas, S. (1986) On the antiquity of cancer: from Hippocrates to Galen. In: Retsas, S. ed. Palaeo–oncology: the antiquity of cancer. London: Ferrand Press, 41–53.

Wattenberg, L.W. (1993). Inhibition of carcinogenesis by non–nutrient constituents of the diet. In: Food and Cancer prevention—chemical and biological aspects, edited by Waldron, K.W. Johnson, I.T., and Fenwick, G.R., The Royal Society of Chemistry, Cambridge, U.K., pp. 12–23.

Habtemariam et al., Journal of Ethnopharmacology 40(3): 195–200 (1993).

Okwuasaba et al., Journal of Ethnopharmacology 20(2): 85–106 (1987.

Parry et al., Journal of Ethnopharmacology 22(1): 33–44 (1988).

*Primary Examiner*—Jean C. Witz
*Attorney, Agent, or Firm*—Leonard Bloom

[57] ABSTRACT

*Portulaca oleracea* has been used throughout history for many different medicinal purposes. This invention is directed to the novel use of *P. oleracea* for the treatment of cancer. More specifically it is disclosed that *P. oleracea* has a specific and distinct effect on the inhibition and/or suppression of gastric tumor cell growth in vitro and in vivo. An aqueous extract of *P. oleracea* showed a tumoricidal activity against KATO III (human gastric carcinoma cell line) and COLO 320 HSR cells (human colon adenoma cell line) in a dose-dependent and time-dependent manner, but not against the non-tumorous cell lines, L929 (murine lung connective tissue) and W138 (human lung diploid cell) cells. Subcutaneous injection of six week old CD1 nude mice with COLO 320 HSR cells and subsequently *Portulaca oleracea* extract showed a clear inhibition of tumor growth as compared to the control nude mice which received only COLO 320 HSR cells.

12 Claims, 13 Drawing Sheets

PORTULACA OLERACEA AND TUMOR CELL GROWTH

The present invention relates to the tumoricidal activity of *Portulaca oleracea* extracts. More specifically this invention relates to the suppression of tumor cell growth in vitro and in vivo.

BACKGROUND OF THE INVENTION

Full citations for references appear at the end of the examples section.

*Portulaca oleracea* is found ubiquitously in habitats with warm climate (Habtemariam et al., 1993). It has been used as an edible plant by humans since the prehistoric age. In China, the Philippines, Southeast Asia, and Africa, this wild plant is still consumed as food in various ways (Herklots, 1972). *P. oleracea* is recognized as a quite nutritious vegetable. It includes carbohydrates, amino acids, omega-3 fatty acids (Simopoulos et al., 1992, Mohamed and Hussein, 1994), several vitamins and minerals and many others (Wattenbergs, 1993) (Table 1).

TABLE 1

Composition of *Portulaca oleracea*

1. Noradrenaline
2. Dopa
3. Dopamine
4. Cardiac-glycoside
5. Anthraquinone-glycoside
6. Glucose
7. Sucrose
8. Fructose
9. Coumarin
10. Amino acids
11. Saponins
12. Alkaloids
13. Flavonoids
14. Citric acid
15. Oxalic acid
16. Glutamic acid
17. Asparaginic acid
18. Malic acid
19. Tannic acid
20. Vitamins A, $B_1$, $B_2$, C
21. Catechol
22. Urea
23. Wax
24. Batacyanin
25. K-salt (KCl. $K_2SO_4$, $KNO_3$)
26. $K_2O$
27. Fe**

In some countries, *P. oleracea* has been well known for ages as a medicinal herb. It has been used in the treatment of cardiovascular disease in Jamaica and in the topical application for swellings, bruises, abscesses and boils in Nigeria. In addition, it is known to be effective as an expectorant to treat cough (Vemla et al., 1982). It was also used as a "heart-tonic" and a diuretic. There are reports about the analysis of its composition (Tulloch, 1975, Simopoulos et al., 1992, Mohamed and Hussein, 1994), its influence on muscle (Parry et al., 1987, Parry et al., 1993), its effect on antifertility (Verma et al., 1982), and its efficacy in treating blood sugar levels in diabetics (Kin Y, JP 63,208, 531, published Aug. 30, 1988).

Several plant products are known for their potential for the prevention and treatment of cancer (Retsas, 1986, Huang et al, 1994, Lau et al 1994). However, the influence of *P. oleracea* on cancer has not been reported.

SUMMARY OF THE INVENTION

The present invention relates to the tumoricidal activity of an extract obtained from *P. oleracea*.

According to the present invention there is provided a composition comprising an aqueous extract obtained from *P. oleracea* with tumoricidal activity. This extract may also be obtained following solvent extraction of the plant, preferably leaf tissue.

This invention further relates to a bio-active ingredient form *P. oleracea* having tumoricidal activity.

This invention also provides for a method for the preparation of a tumoricidal extract obtained from *P. oleracea* involving homogenizing the plant in at least one solvent and retaining the aqueous fraction.

This invention also relates to a method of preventing tumor cell growth, preferably stomach tumor cells through the administration of a composition comprising an extract obtained from *P. oleracea*.

This invention also relates to a method of treating tumor cells, preferably stomach tumor cells through the administration of a composition comprising an extract obtained from *P. oleracea*.

This invention also provides for pharmaceutical compositions comprising an aqueous extract obtained from *P. oleracea*, and a suitable carrier.

Another aspect of an embodiment of this invention is a method for the treatment of tumor cells by administering a suitable amount of the composition or bio-active ingredient described above.

Although the present invention is exemplified by the treatment of stomach cancer cells, in practice any tumor cell can be treated with the extract of this invention.

BRIEF DESCRIPTION OF THE DRAWINGS

These and other features of the invention will become more apparent from the following description in which reference is made to the appended drawings wherein:

FIG. 2A: *P. oleracea* extract-treated, FIG. 2B: no extract-treated control.

The proteins were stained with Coomassie Blue. Lane M: molecular weight standard in KD, Lane 1: no serum, Lane 2: no extract, Lane 3: 0.2 mg/ml, Lane 4: 0.4 mg/ml, Lane 5: 0.8 mg/ml, Lane 6: 1.6 mg/ml, Lane 7: 3.2 mg/ml of *P. oleracea* extract-treated. Arrows indicate the protein bands that were decreased by the treatment of *P. oleracea* extract.

Figure 6:

FIG. 6 shows DNA fragmentation analysis of KATO III cells after treatment of *P. oleracea* extract. KATO III cells (1×10⁶) were collected 16 hours after incubation with various concentrations of *P. oleracea* extract. The genomic DNA was isolated and electrophoresed on 1.5% of agarose gel. DNA was stained with ethidium bromide. Lane M: molecular weight standard in Kb, Lane 1: no extract treated control, Lane 2: 0.2 mg/ml, Lane 3: 0.4 mg/ml, Lane 4: 0.8 mg/ml, Lane 5: 1.6 mg/ml of *P. oleracea* extract-treated.

Figure 7:
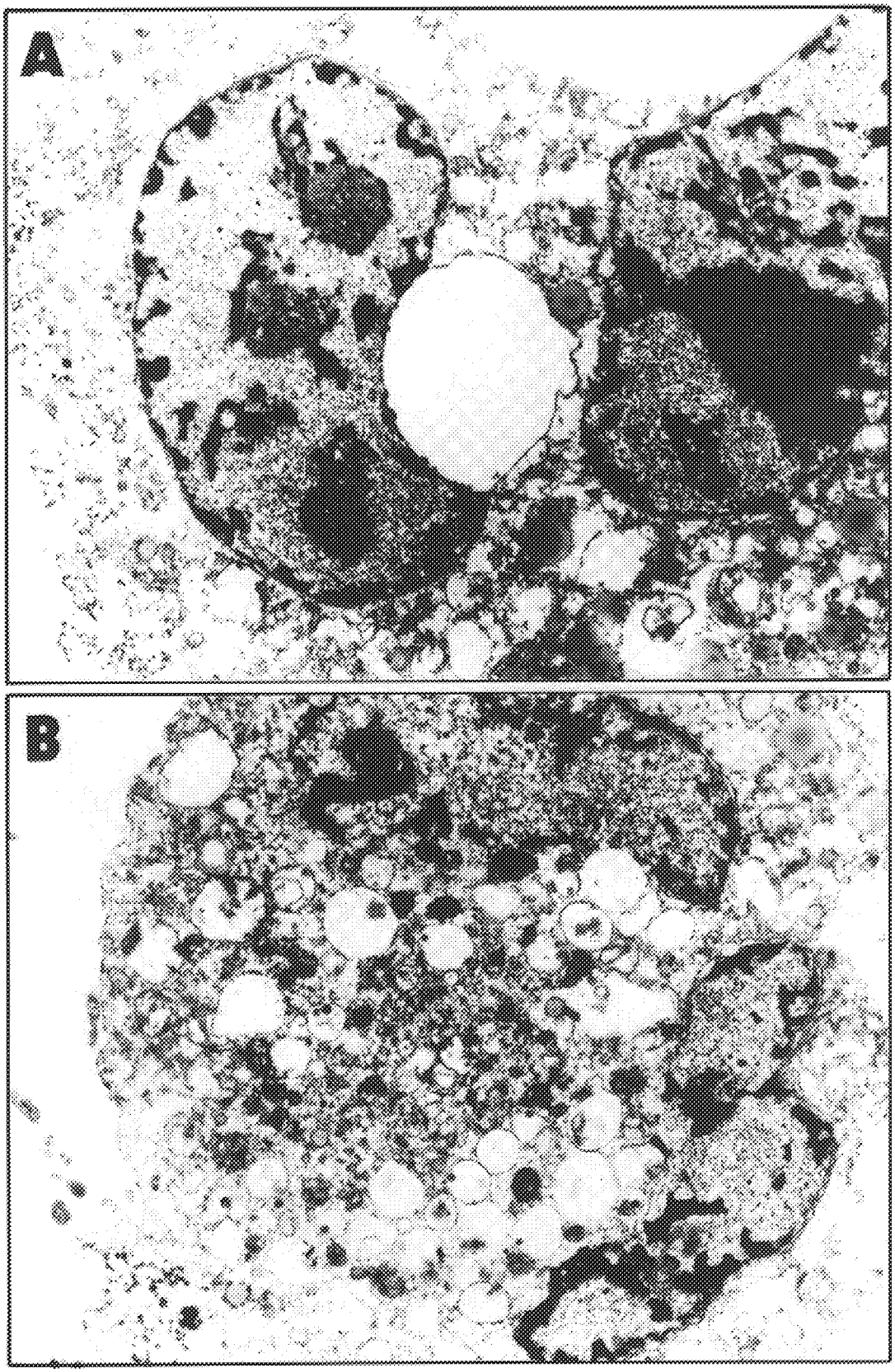

FIGS. 7A–7B are electron microscopic pictures of KATO III and COLO 320 HSR cells after treatment of *P. oleracea* extract. KATO III (FIG. 7A) or COLO 320 HSR cells (FIG. 7B) were cultured for 24 hours with *P. oleracea* extract (0.6 mg/ml) and fixed. Magnification 18000×.

FIGS. 8A–8B are electron microscopic pictures of L929 (FIG. 8A) or W138 (FIG. 8B) cells after treatment of *P. oleracea* extract. L929 or W138 cells were incubated for 24 hours with *P. oleracea* extract (0.6 mg/ml) and fixed. Magnification 15000×.

Figure 9:
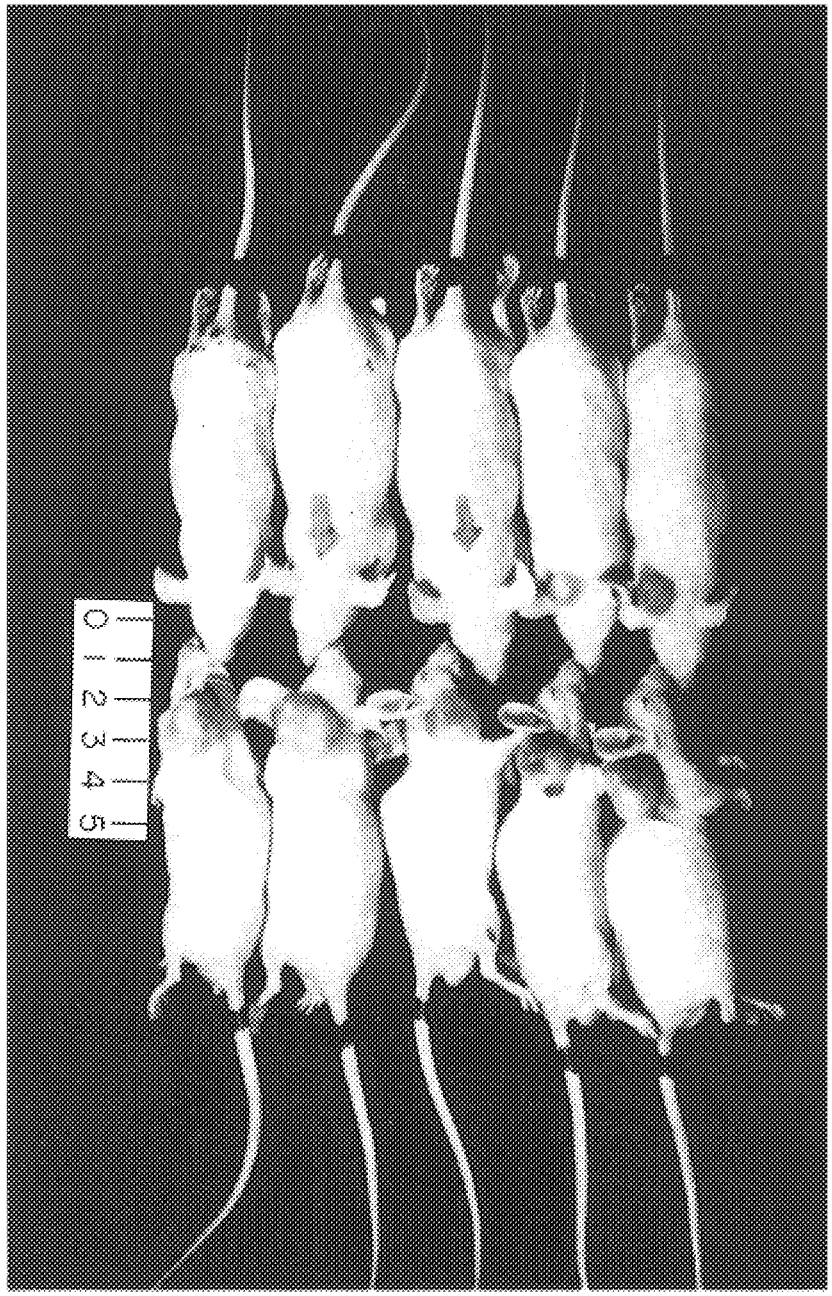

FIG. 9 is the inhibition of tumor growth after treatment of *P. oleracea* extract in CD1 nude mice induced by COLO 320 HSR cells. Six-week-old CD1 nude mice received COLO 320 HSR cells (1×10⁸) and *P. oleracea* extract (5 mg/day/mouse; 0.05 mg/mg/day) for 10 days (right side). As a control, the mice received COLO 320 HSR cells (1×10⁷) and same volume of 10% ethanol without *P. oleracea* extract (left side). The picture was taken at 30 days after tumor cell injection.

FIGS. 10A–10B are pictures of isolated tumor after treatment of *P. oleracea* in CD1 nude mice induced by COLO 320 HSR cells. The tumor was isolated from tumor-induced CD1 nude mice which was treated with *P. oleracea* extract and the picture was taken as described in the legend to FIG. 9. FIG. 10A. left side: no extract-treated control, right side: extract-treated with 0.05 mg/gm/day aqueous extract. FIG. 10B, left side: no extract-treated control, right side: extract-treated with 0.25 mg/gm/day of the aqueous extract.

Figure 11:
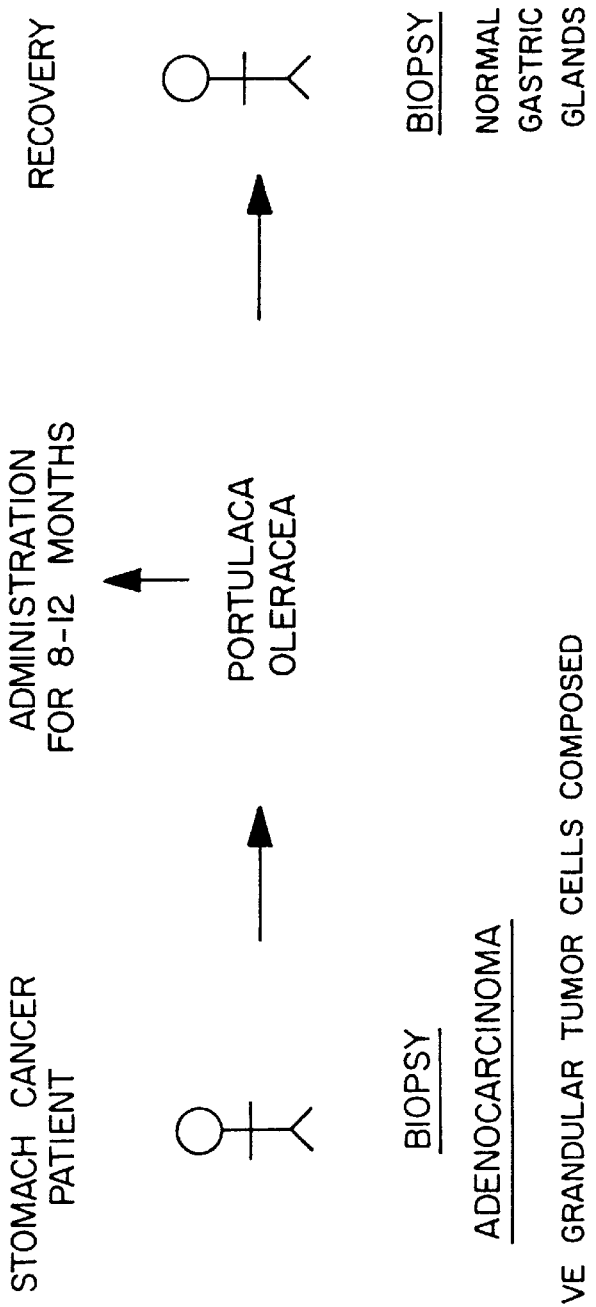

FIG. 11 is an outline of the experimental protocol of the in vivo treatment of a stomach cancer patient treated with *P. olearcea* extract.

Figure 12:
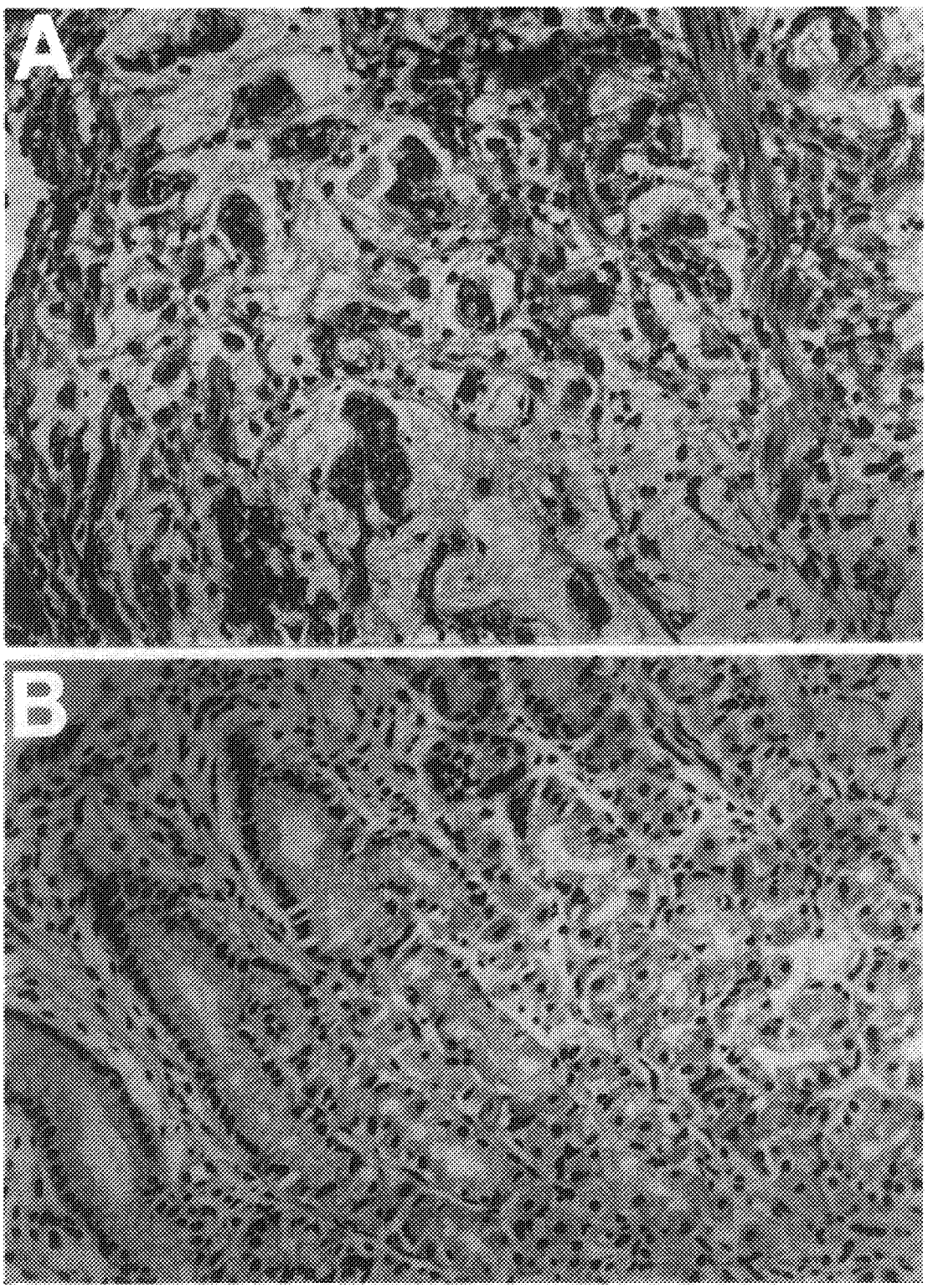

FIGS. 12A–12B are light micrographs of stained stomach cells obtained from a stomach cancer patient before treatment (FIG. 12A) or after 8–12 months treatment (FIG. 12B) with 0.007–0.015 mg/gm/day *P. oleracea* extract.

Figure 13:
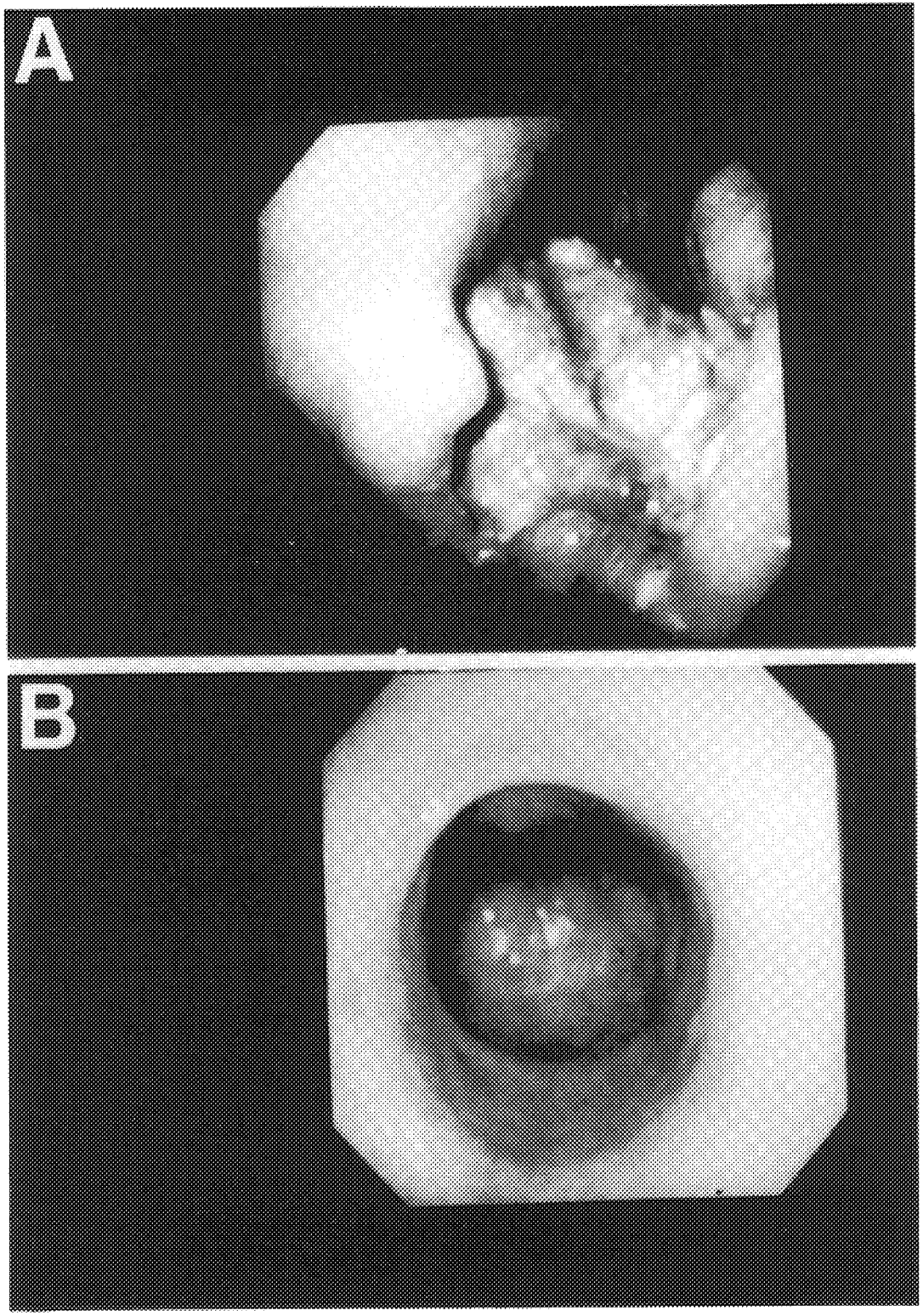

FIGS. 13A–13B are gastroscopic photographs obtained of the atrium of the stomach of a stomach cancer patient before treatment (FIG. 13A) and after 8–12 months treatment (FIG. 13B) with 0.007–0.015 mg/gm/day *P. oleracea* extract.

DESCRIPTION OF PREFERRED EMBODIMENT

The present invention is directed to the tumoricidal effect of *P. oleracea* extracts. This invention also provides for pharmaceutical compositions and related methods for the use of the extract from *P. oleracea* as an anti-cancer agent.

According to the present invention, by "aqueous extract" or "extract" it is meant the aqueous fraction following the extraction of *P. oleracea*. Such an aqueous fraction may be obtained following one or more solvent extraction steps of plant or leaf tissue.

By "tumoricidal activity" it is meant the selective cytotoxic effect of the *P. oleracea* aqueous extract on tumor cells, exemplified by gastric carcinoma and colon adenoma cell lines, but not non-tumor cells, exemplified by lung connective tissue, and lung diploid cell lines. Based on the action of the oncogenes involved in the cancerous development in these cells, the aqueous extract would also have an effect on tumoricidal activity in tumors associated with liver and kidney cells as well.

Figure 3:
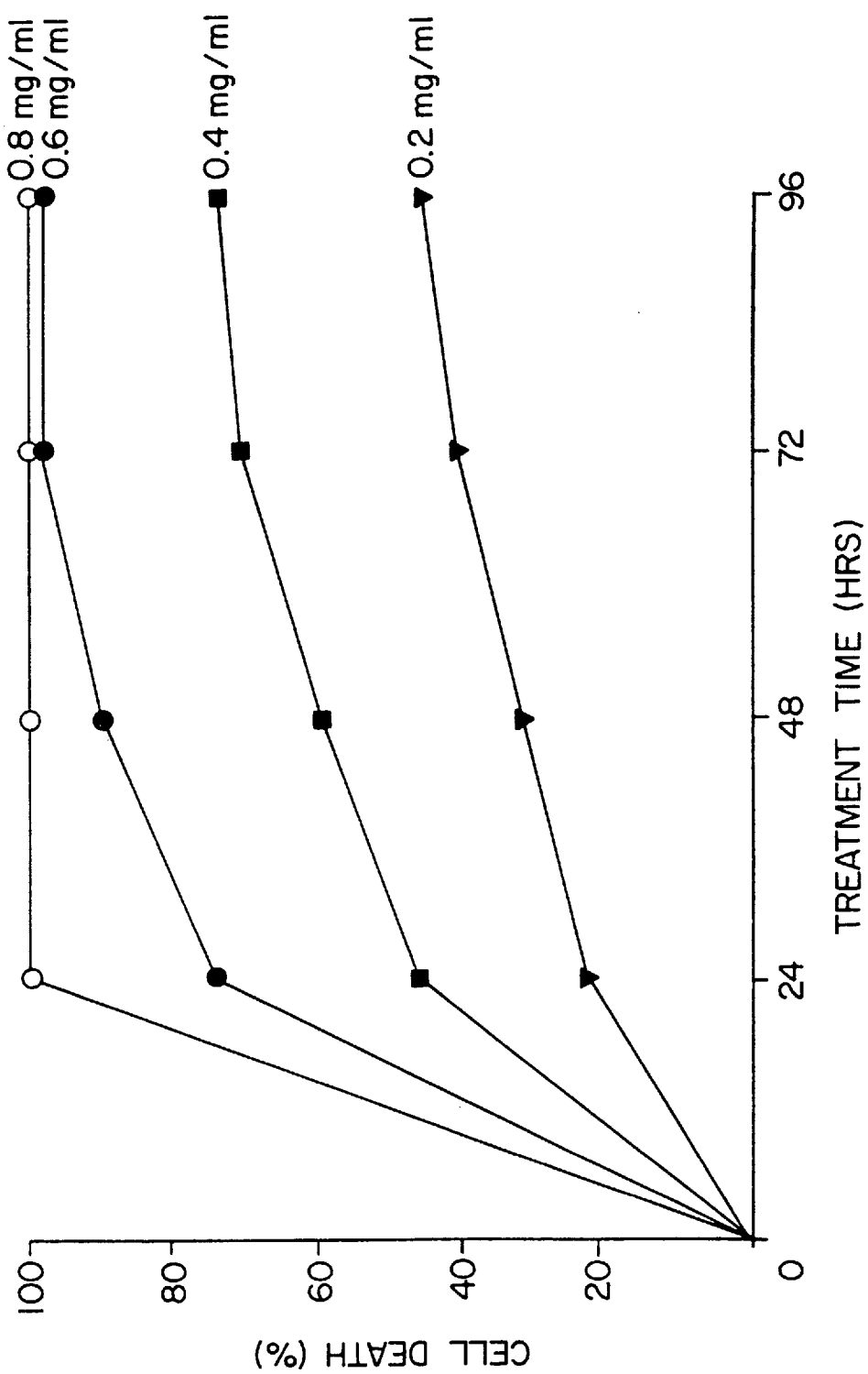
FIG. 3 is the dose and time-dependent cytotoxic effect of *P. oleracea* extract on KATO III cells. KATO III cells ($2.5 \times 10^4$) in 100 µl of media in 24 well plate were cultured for 48 hours. *P. oleracea* extract at different concentrations was added and incubated for 24, 48, 72 and 96 hours and the percent of cell death calculated.
Figure 4:
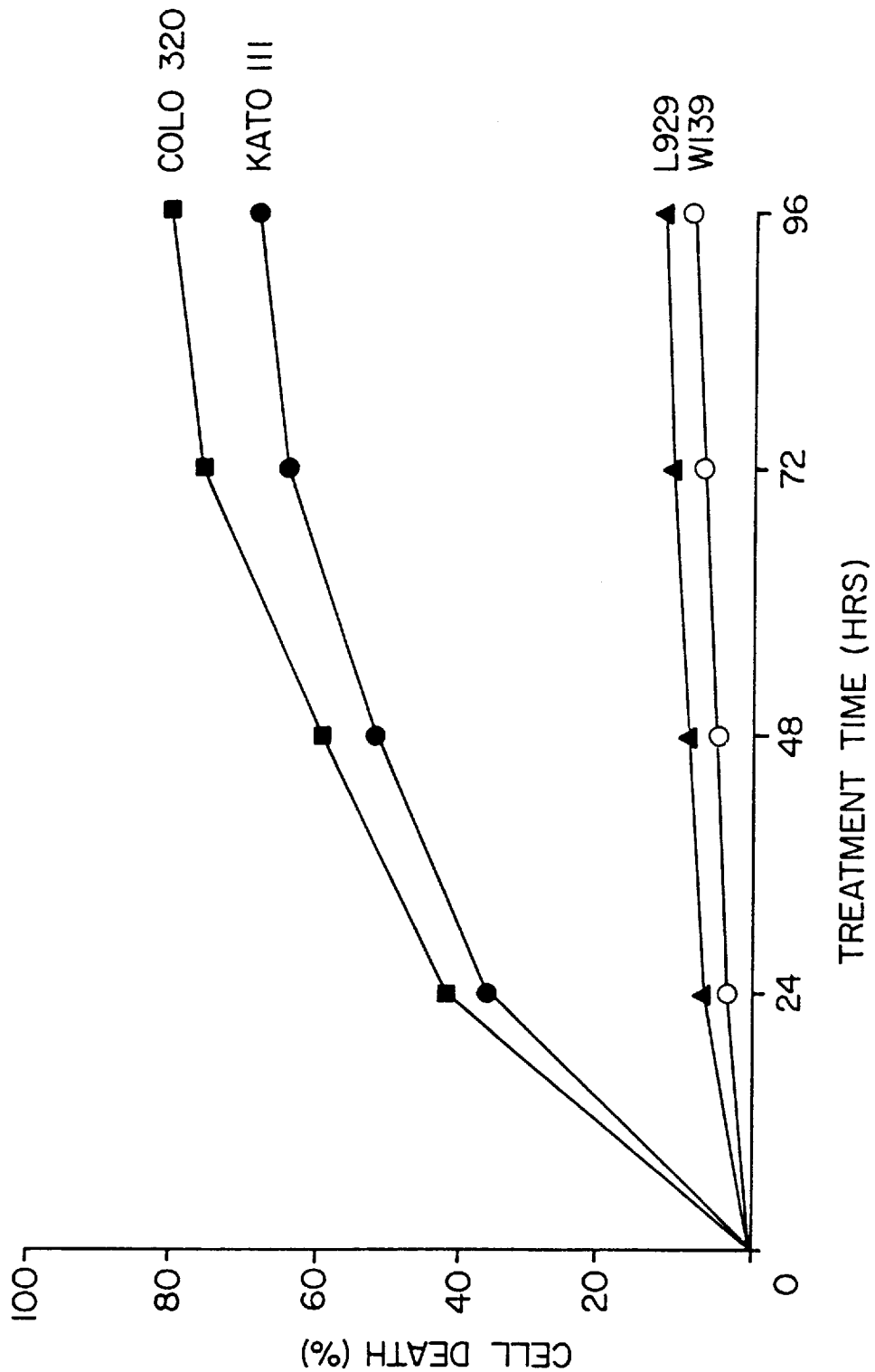
FIG. 4 is the cell-specificity of cytotoxic effect of *P. oleracea* extract. KATO III, COLO 320 HSR, L929, or W138 cells ($2.5 \times 10^4$) in 100 µl of media in 24 well plate were cultured for 48 hours. *P. oleracea* extract (0.4 mg/ml) was added and incubated for 24, 48, 72, and 96 hours and the percent of cell death calculated.

It is widely known that *P. oleracea* is a very valuable plant for many different medicinal purposes and as a supply of various nutrients (Tulloch, 1975, Verma et al., 1982. Parry et al., 1987, Simopoulos et al., 1992, Parry et al., 1993). In our search for therapeutic agents from natural sources with a potential for the treatment of cancer, we investigated anti-tumor activities of *P. oleracea*. We found that *P. oleracea* extract has an anti-tumor activity on tumor cell lines such as COLO 320 HSR and KATO III. *P. oleracea* extract showed dose and time-dependent cytotoxic activity on these cells (FIG. 3). However, *P. oleracea* extract did not have cytotoxic effect on normal fibroblast cell lines such as L929 and W138 (FIG. 4). This result suggests that *P. oleracea* extract has a specific cytotoxic effect on tumor cells, but not normal cells. When the cytotoxic activity of *P. oleracea* extract was compared with other plant extracts, *P. oleracea* showed the strongest tumoricidal activity among 5 plant extracts that were tested (see Example 1).

Mechanism of Cell Death

Apoptosis is a distinct form of cell death (William et al., 1991, Kerr et al., 1994) and a variety of anti-cancer drugs have been shown to induce extensive apoptosis (Hickman, 1992). In order to study the precise mechanism of anti-tumor effect of *P. oleracea* extract, inter-nucleosomal DNA fragmentation of KATO III cells, after treatment with the extract, was examined since DNA fragmentation is one of the hallmarks of apoptosis (Anderson et al, 1994). However, no fragmentation of genomic DNA was shown (FIG. 6). We also observed the morphology of extracted-treated cells and found that the cells showed cytoplasmic vacuoles with disintegrated cell membrane, which is different from the morphology of apoptosis.

The morphological changes were shown to be similar to the effect of dopamine on lymphoid tumor cell lines, which revealed cytoplasmic swelling and vacuolization and nuclear pycnosis (Braesch-Anderson et al., 1992). *P. oleracea* contains dopamine as a major constituent. It may also be possible that dopamine plays a role as an active compound for the anti-tumor effect. Thus we further examined the mechanism of cytotoxic effect of this plant extract. When we analyzed protein synthesis of KATO III cells after treatment of *P. oleracea* extract, total protein synthesis was generally decreased. Specifically, three proteins with a molecular weight of 85,000 (P85), 64,000 (P64), and 40,000 (P40) daltons were decreased in amount (FIG. 5), and likely to be inhibited in a dose dependent manner of *P. oleracea* extract. This result imply that these proteins might be involved in tumor cell proliferation.

Based on these observations, and without wishing to be bound by theory, it appears that *P. oleracea* has a specific cytotoxic effect on tumor cells in vitro and in vivo. The mechanism of action appears to be due to a cell-specific cytotoxic effect.

In Vivo Studies

Whether *P. oleracea* extract could also inhibit tumor growth in vivo was also examined. Nude mice were induced to form tumors with COLO 320 HSR cells. In mice treated with COLO 320 HSR cells and with a *P. oleracea* extract, tumor growth was clearly inhibited (Table 2). The treatment with 5 mg of *P. oleracea* extract per day for 10 days depressed the size of tumor in the range of 0.4 cm at 30 days after the tumor cell inoculation. In contrast, the tumor size of untreated animals was in the range of 1.4 cm. The treatment with 1 mg per day showed less effect on tumor regression. This result shows that the greater the amount of *P. oleracea* extract, the greater the inhibition of tumor growth in vivo.

The bio-active ingredient of the water-extract obtained from *P. oleracea* can be administered to effect treatment of tumor cells. Such a bio-active ingredient would be formulated as a pharmaceutical composition in the presence of a suitable carrier such as those used for the preparation of, but not limited to, solid, particulate or suspension formulations for tablets, capsules, elixir, parenteral, suppository, transdermal or topical administration. Suitable carriers include, but are not limited to magnesium stearate, starch, lactose, sucrose and cellulose for the formulation of tablets; aqueous gums, celluloses, silicates or oils and the dispersion or suspension of bio-active ingredient into gelatin capsules; liquid carriers including syrups, glycerin, peanut or olive oil, ethanol, saline and water in the case of elixirs; parenteral compositions could be formulated with a solution or suspension of the bio-active ingredient in a sterile aqueous carrier or parenterally acceptable oil such as polyethylene glycol, polyvinyl pyrrolidine, lecithin, arachis oil, sesame oil or the like; binding, and/or lubricating agents, for example polymeric glycols, gelatins or coca butter or other low melting vegetable or synthetic waxes or fats in the case of suppository compositions; aqueous or non-aqueous vehicles such as creams, ointments, liposome preparations, lotions, paste or medicated plaster, patch or membrane or the like for typical transdermal applications; and, for topical administration, pharmaceutical typically formulations include solutions, suspensions, ointments and solid inserts for example water, water miscible solvent mixtures including lower alkanols, or vegetable oils, emulsifying, preserving wetting and bodying agents such as polyethylene glycols, and antibacterial components. Furthermore, the bio-active ingredient may be administered in a timed release dosage unit form to permit sustained release of the bio-active ingredient. Such carriers may include glyceryl monosterate or glyceryl distearate, alone or in combination with a wax.

The pharmokinetic properties of the bio-active component must be determined to formulate dosing regimes that induce tumoricidal activity without significant adverse side effects. The bio-active ingredient may also be administered singly or in combination with other bio-active agents of interest.

Suitable dosages of the bio-active ingredient of *P. oleracea* in a suitable pharmaceutical carrier for use in the treatment of tumorous cell growth in mammals including humans, according to the present invention, should not exceed about 1.0 mg/gm body weight. Preferably the dosage is in the range of 0.05–0.5 mg/gm body weight. It will be appreciated that the actual preferred dosages of the bio-active ingredient being administered will vary according to the particular composition formulated, the site and host being treated, and the mode of adminstration.

Examples

Animals

Six week-old CD1 nude mice (nu/nu) were purchased from Charles River, St-Constant, Quebec, Canada and maintained in a specific pathogen free (SPF) facility at the University of Calgary.

Extraction of *P. oleracea*

Figure 1:
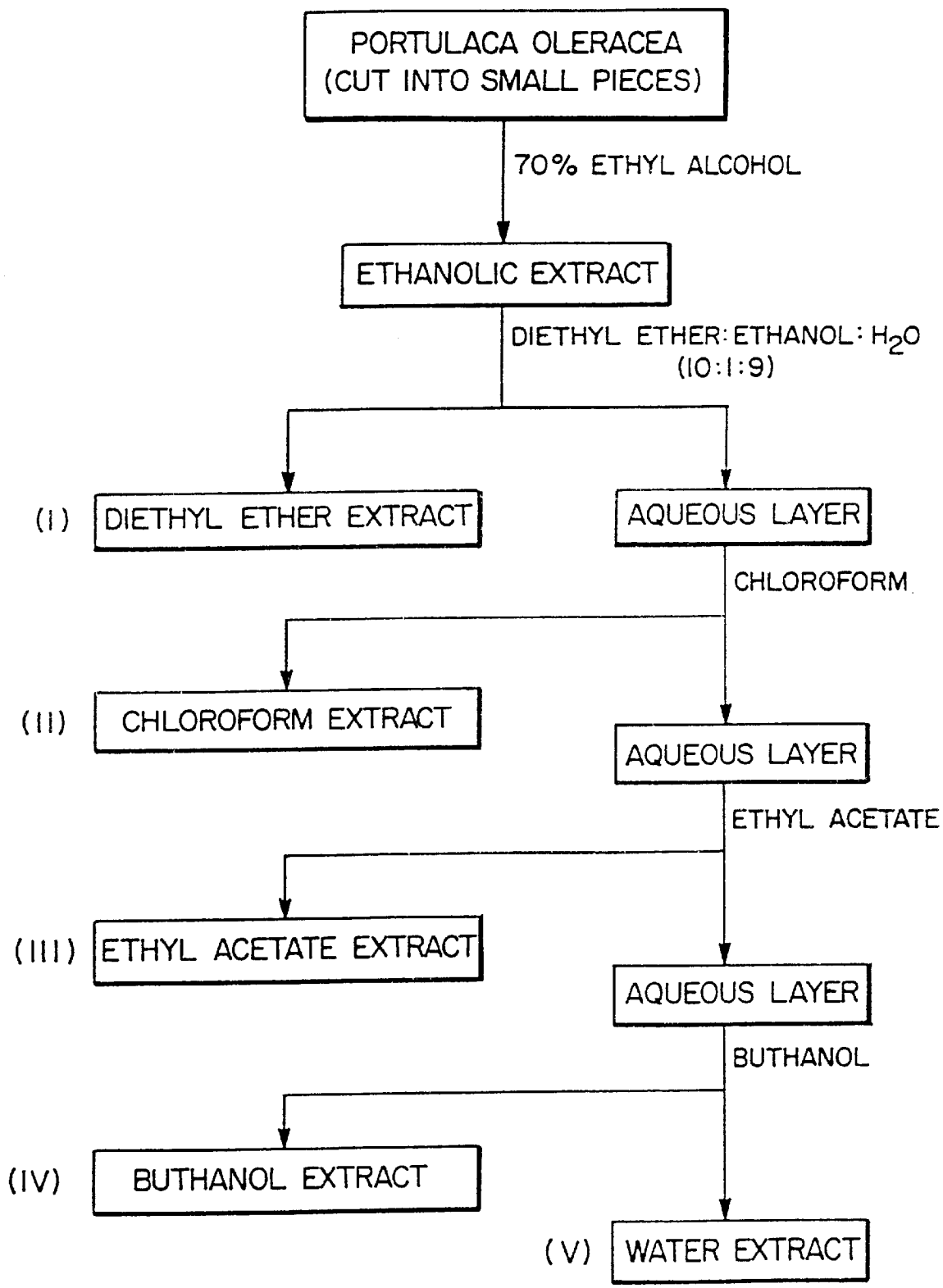
FIG. 1 is the procedure for extraction of *P. oleracea* extract. Whole plant was sliced into small pieces and homogenized in 70% ethanol (100 w/v). The homogenate was concentrated and dissolved in a solvent containing diethyl ether ethanol and water (10:1:9). The aqueous layer was further extracted progressively through chloroform ethylacetate and butanol. The final aqueous layer, the aqueous extract, was freeze-dried, dissolved in PBS prior to use.

Whole plants were washed, sliced into small pieces, and extracted as shown in FIG. 1. Briefly, the sliced plant was homogenized in 75% ethanol at a ratio of 10% (w/v). The homogenates were filtered and concentrated using a rotatory evaporator. The concentrated extract was dissolved in a solvent containing diethyl ether, ethanol and water at the ratio of 10:1:9, and then partitioned between diethyl ether and water. The aqueous layer was further extracted using chloroform, ethylacetate, and butanol in a orderly fashion. The separated final aqueous layer was freeze-dried. This aqueous extract of *P. oleracea* was dissolved in phosphate buffered saline (PBS) and filtered through a 0.22 $\mu$m membrane filter.

Cell Culture

KATO III (human gastric carcinoma cell line), COLO 320 HSR (human colon adenocarcinoma cell line), W138 (human lung diploid cells), and L929 (murine lung connective tissue) were obtained from the American Type Culture Collection (ATCC). The cells were grown in RPMI 1640 (Gibco BRL, Gaithersberg, Md., USA) supplemented with 10% heat-inactivated fetal bovine serum (FBS) and maintained in a 5% $CO_2$ incubator at 37° C.

Cytotoxicity Assay

Growth of tumor cells was evaluated by a trypan blue incorporation assay. In brief, KATO III cells in 100 $\mu$l of media ($2.5 \times 10^5$ cells/ml) were placed in a 24 well microtest plate (Falcon no:3047, Beckton Dickinson Co., Lincoln Park, N.J.) and cultured in a 5% $CO_2$ incubator at 37° C. for 48 hours. Extracts of *P. oleracea, Taraxacum platicarpium, Fagopyrum esculentum, Prunella asiatica, Veratrum album* were added to the cell suspension and incubated the cells for 1 to 4 days. The cells were centrifuged and the cell pellet was suspended in 100 ul of RPMI medium and 0.2% trypan blue solution. Untreated cells were used as a control. The number of dead cells was counted under a microscope and calculated using the following equation:

$$\% \text{ of cell death} = \frac{\text{No. of stained cells}}{\text{No. of total examined cells}} \times 100$$

Electron Microscopy

To examine morphological changes, the cells treated with or without *P. oleracea* extract were fixed with 2.5% glutaraldehyde in 0.1M cacodylate buffer (pH 7.4) at 4° C. for 1 hour and washed 2 to 3 times with the same buffer to remove excess aldehyde prior to second fixation. One percent of osmium tetraoxide ($OsO_4$) in 0.1M cacodylate buffer was used for post fixation at 4° C. for 1 hour. These fixed cells were dehydrated using a series of concentrations of ethanol to remove all free water, then embedded in Epon epoxy resin, and polymerized at 45° C. in an oven for 18 to 24 hours. Ultrathin sections were made by cutting with an ultramicrotome (Riechert-Jung, Austria). Sample sections were stained with uranyl acetate and lead citrate, and examined with a Hitachi H-7000 electron microscope (Hitachi LTD, Kaka works, Katsuda city, Japan).

Protein Analysis

KATO III cells ($1 \times 10^6$ cells) were harvested 16 hours after incubation with *P. oleracea* extract at various concentrations (0.2, 0.4, 0.8, 1.6, 3.2 mg/ml). After washing with PBS, the cells were pelleted and dissolved in 40 ul of lysis buffer (4% SDS, 73 mM Tris-CI, pH 6.8, 10 mM DTT). The cell lysates were centrifuged at 55,000 rpm (Ti 100, Beckmann) for 1 hour at 4° C. After taking out the supernatant, protein concentration was measured using Bio-Rad protein assay kit (BioRad, Richmond, Calif., USA). The protein samples were mixed with dye solution (0.25% bromophenol blue, 25% Ficoll®), boiled for 2 mins. and loaded on a 10% SDS-polyacrylamide gel. After gel electrophoresis, protein bands were visualized by staining with a 0.1% Coomassie Blue solution.

DNA Fragmentation Analysis

KATO III cells ($1 \times 10^6$) were collected 16 hours after treatment of various concentrations of P. oleracea extract (0.2, 0.4. 0.8, 1.6 mg/ml). The cells were washed with PBS, centrifuged at 200×g for 10 mins. and lysed in a lysis buffer (0.5% sodium lauryl sarcosinate, 0.5 mg/ml proteinase K, 10 mM EDTA and 50 mM Tris-CI, pH 7.5). The samples were extracted once with phenol/chloroform and then chloroform. Genomic DNA was precipitated with 2 volumes of ethanol in the presence of 3M sodium acetate (pH 5.2) and washed with 70% ethanol. The pellet was dried in a vacuum drier and dissolved in TE (10 mM Tris-Cl, 1 mM EDTA, pH 8.0). RNA was removed by RNase (20 ug/ml) treatment at 37° C. for 1 hour and 3 ug of DNA was loaded on a 1.5% (w/v) agarose gel. Electrophoresis was carried out and DNA was visualized by ethidium bromide staining.

In Vivo Treatment using P. oleracea Extract

CD1 nude mice (5 mice/group) were injected subcutaneously in the neck with a single dose of COLO 320 HSR cells ($1 \times 10^7$ cells). The extract of P. oleracea (1 mg or 5 mg in 100 $\mu$l of 10% ethanol) was given intraparenteraly from the same day for 10 days consecutively. Control mice (n=5) were injected with the same volume of 10% ethanol. The size of tumors was measured on the day of 10, 20, 25, and 30 after tumor cell injection.

Example 1: Cytotoxic Effect of P. oleracea Extract on Tumor Cells in Vitro

Figure 2:
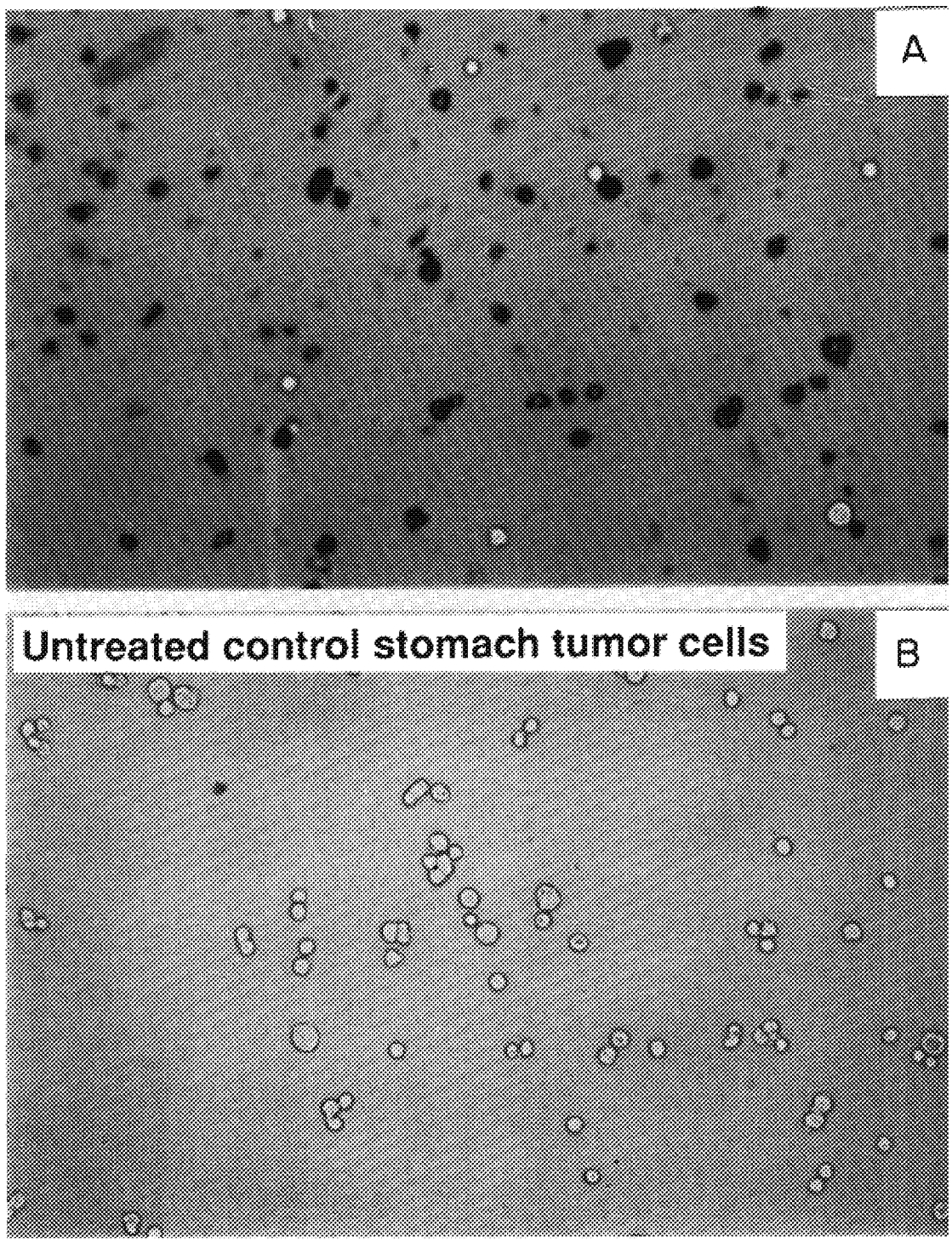
FIGS. 2A–2B show the cytotoxic effect of *P. oleracea* extract on KATO III cells. KATO III cells ($2.5 \times 10^4$) in 100 µl of media in 24 well plate were cultured for 48 hours *P. oleracea* extract was added and incubated for 24 hours. Live cells were evaluated by a trypan blue incorporation assay.

To determine whether or not a P. oleracea extract had any effect on cultured tumor cells, cytotoxic activity of P. oleracea extract against KATO III cells was examined at different incubation hours after treatment. P. oleracea extract contains a tumoricidal activity against KATO III cells (FIG. 2 and 3). Most of the extract-treated cells were dead (FIG. 2B) compare to non-treated cells (FIG. 2A). The incubation of these cells with P. oleracea extract caused cell death in a dose-dependent and time-dependent manner (FIG. 3). The extract at the concentration of 0.6 mg/ml for 24 hours of incubation killed 74% of KATO III cells for 48 hours 92% and 72 hours 100%. The higher concentration of the extract showed higher cytotoxic activity. To compare the cytotoxic activity of P. oleracea with other plant extracts we tested the cytotoxic effect of several different kinds of plant extract on KATO III cells. P. oleracea extract showed the highest inhibitory activity against KATO III cells showing 100% of cell killing after 24 hours of incubation. Under the same condition, Taraxacum platicarpurn, Fagopyrum esculentum, Prunella asiatica, and Veratrum album showed 0, 8, 18, 32% of cell death, respectively. We also examined the specificity of the cytotoxic effect of P. oleracea extract on different tumor cells. P. oleracea extract killed KATO III cells (70%) and COLO 320 HSR cells (80%), but did not greatly affect much L929 and W138 cells showing less than 20% of killing (FIG. 4).

Example 2: Mechanism of Action

Figure 5:
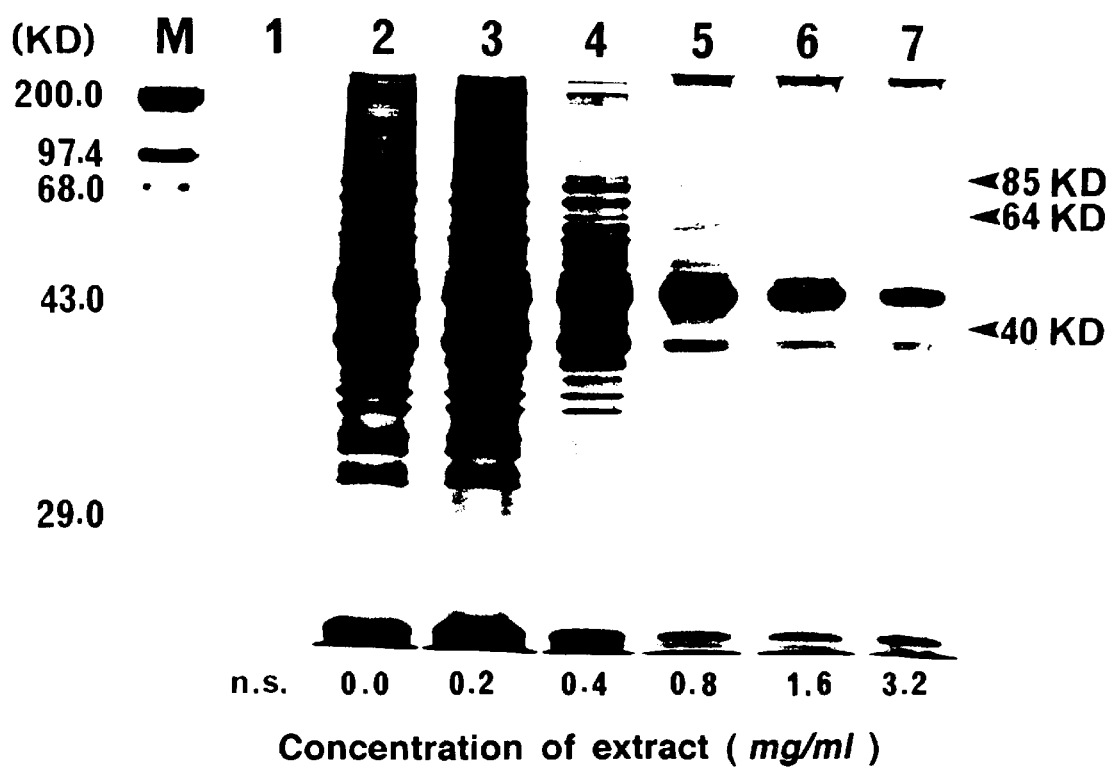
FIG. 5 is the total protein analysis of KATO III cells after treatment of *P. oleracea* extract. KATO III cells (1×10⁶) were collected 16 hours after incubation with *P. oleracea* extract at various concentrations (0.4, 0.6, 0.8, 1.6, 3.2 mg/ml). Lysates were prepared and separated on 10% SDS-PAGE.

To see whether P. oleracea extract has any effect on the specific inhibition of protein synthesis of tumor cells which may lead to cell death, we examined the pattern of protein synthesis after the treatment of KATO III cells with the extract (FIG. 5). In general, the protein synthesis was significantly decreased at the increased dosage of P. oleracea extract. Three specific proteins i.e. P40, P64, and P85 were apparently inhibited at dosages of 0.8 and 1.6 mg/ml of the extract. This result suggests that these proteins may be involved in the proliferation of tumor cells.

To see whether P. oleracea extract-induced cell death is due to apoptosis, we examined the fragmentation of genomic DNA of KATO III cells after the treatment of the extract since DNA fragmentation is one of the hallmarks of apoptosis. We found that there is no fragmentation of genomic DNA regardless of duration of the treatment and dosage of the extract (FIG. 6). Without wishing to be bound by theory, this result indicates that KATO III cell death may not be due to apoptosis but probably due to cell-specific cytotoxic effects.

Figure 8:
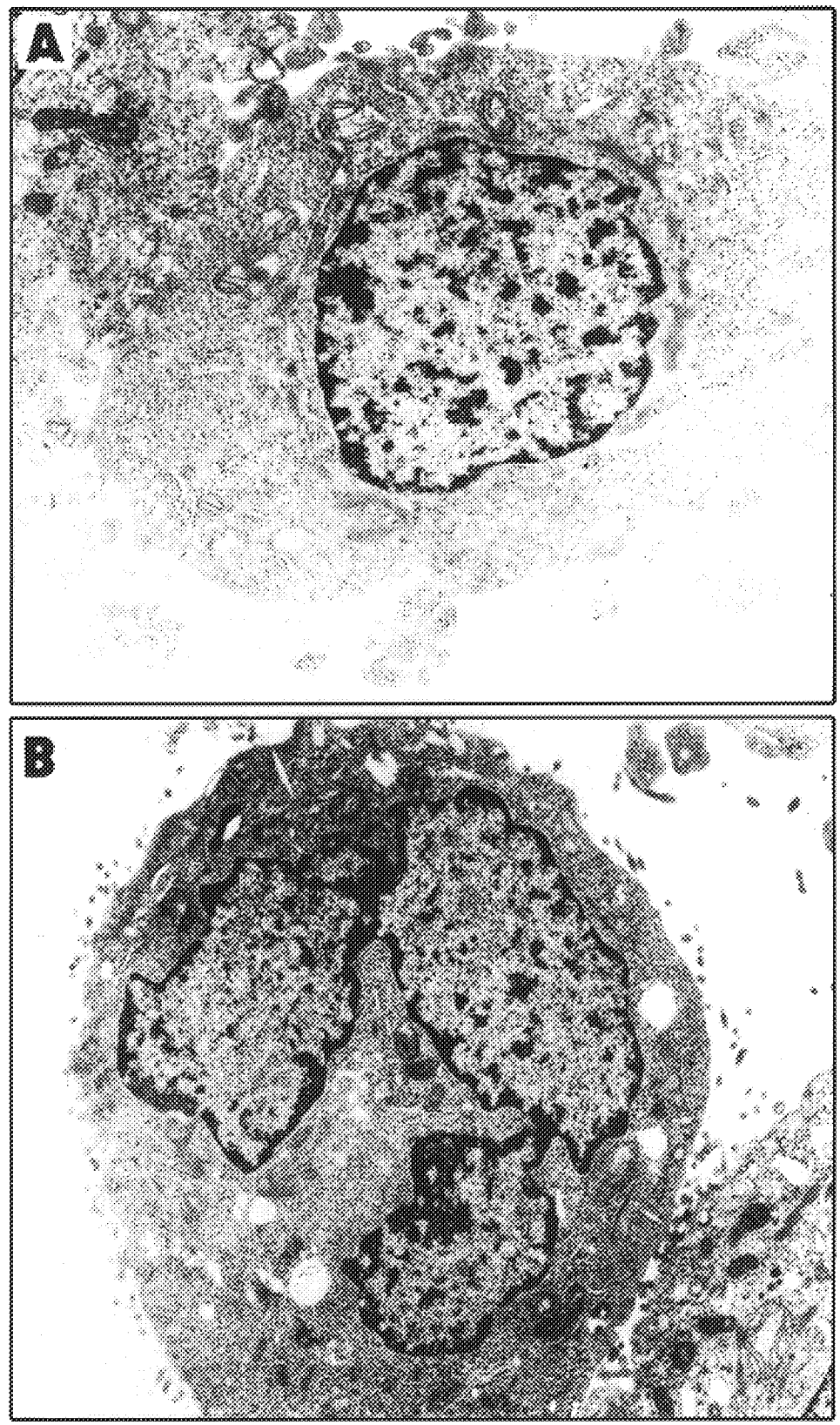

The cell-specific cytotoxicity was confirmed by electron microscopic examination. The extract-treated KATO III cells revealed numerous cytoplasmic vacuoles of various sizes with disintegrated membrane (FIG. 7), while the same extract-treated L929 or W138 cells did not show any morphological changes (FIG. 8).

Example 3: Inhibition of Tumor Growth by P. oleracea Extract in Vivo

Figure 10:
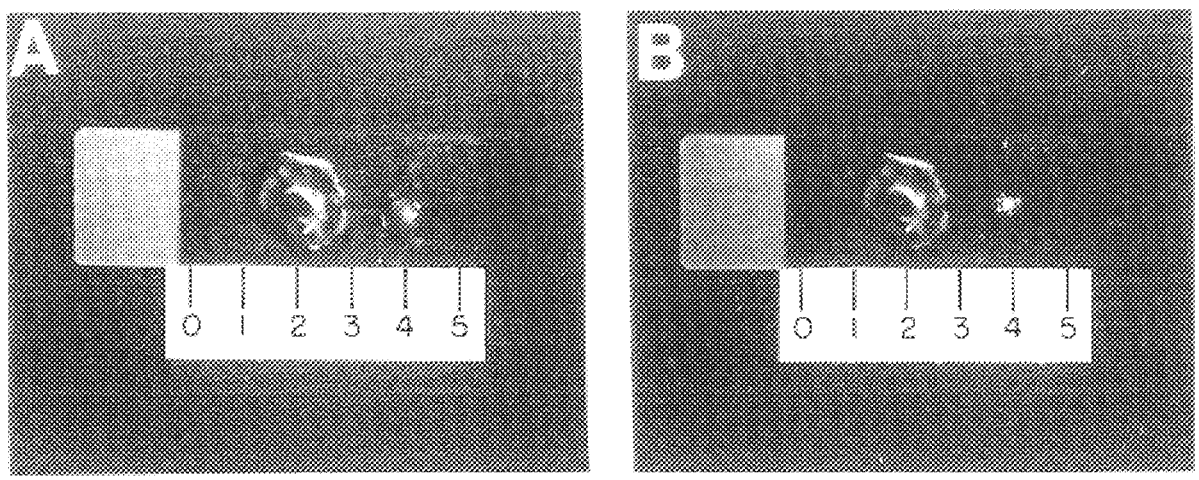

To examine the anti-cancer effect of P. oleracea extract in vivo, six week-old CD1 nude mice (nu/nu) were injected subcutaneously in the neck with COLO 320 HSR cells and subsequently P. oleracea extract (5 mg/day) daily for 10 days. We found that the mice showed only minimum sign of tumors (0.02 cm at 10 days, 0.05 cm at 20 days, 0.1 cm at 30 days after injection) (FIGS. 9 and 10 and Table 2). In contrast, the control mice which received COLO 320 HSR, but not treated P. oleracea extract, developed distinct tumors by the 10th day which continued growing. The mean size of tumor was 0.53 cm at 10 days. 1.24 cm at 20 days, and 1.45 cm at 30 days after injection. This result indicates that P. oleracea extract clearly inhibits tumor growth in vivo.

TABLE 2

Effect of Portulaca oleracea on a tumor growth

| Days after tumor cell injection | Untreated positive control mice | Tumor Size (cm) 1 mg-treated mice (0.05 mg/gm) | 5 mg-treated mice (0.25 mg/gm) | 10 mg-treated mice (0.5 mg/gm) |
|---|---|---|---|---|
| 10 | 0.53 | 0.12 | 0.02 | 0.0 |
| 20 | 1.24 | 0.31 | 0.05 | 0.0 |
| 30 | 1.45 | 0.50 | 0.10 | 0.0 |

Nude mice (5 mice/group) were injected subcutaneously in the neck with COLO 320 HSR cells ($1 \times 10^8$). The value is the mean of the tumor sizes of five samples/group.

Example 4: Treatment of Human Stomach Tumor Growth using P. oleracea Extract

A stomach cancer patient at the terminal stage of illness was administered P. oleracea extract for 8–12 months (see protocol, FIG. 11). The dosage of P. oleracea administered during this treatment period was between 500–1000 mg/day (0.007–0.015 mg/gm/day).

Histological examination of biopsied tissues obtained from cancerous lesions of the stomach prior to treatment with P. oleracea revealed abortive granular cells composed of large hyperchromatic nuclei with clear eosinophilic cytoplasm. Furthermore, these cells floated in abundant extracellular mucous see FIG. 12a. Following the treatment period, histological examination revealed normal stomach cells (FIG. 12b).

Gastroscoptic examination of the stomach of the cancer patient prior to treatment with *P. oleracea* indicated irregular, marginated ulcerating and partial infiltrating lesions in the atrium (FIG. 13a). Following treatment with *P. oleracea* (FIG. 13b) the atrium appears normal.

This result demonstrates the efficacy of in vivo tumor cell treatment using *P. oleracea* extract.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

REFERENCES

Anderson, K. M. Harris, J. E. and Bonomi, P. (1994). Potential applications of apoptosis in modifying the biological behaviour of therapeutically refractory cancers. Medical Hypotheses 43:207–213.

Braesch-Anderson, S. m. Paulie, S., and Stamenkovic, I. (1992). Dopamin-induced lymphoma cell death by inhibition of hormone release. Scand. J. Immunol. 36:547–553.

Habternariam. S., Alan, I., Harver, L., and Waterman, P. G. (1993). The muscle relaxant properties of *Portulaca oleracea* are associated with high concentrations of potassium ions. J. Ethnopharm. 40:195–200.

Herklots, G. A. C. (1972). Purslane: vegetable in Southeast Asia, South China Morning Post Ltd., Hong Kong.

Hickman, J. A. (1992). Apoptosis induced by anti-cancer drugs. Cancer Metastasis Rev. 11: 121–139.

Huang. M. T., Ho, C. T., Wang, Z. Y., Ferraro, T., Lou, Y. R., Stauber, K., Ma, W., Georgiadia, C., Laskin, J. D., and Conney, A. H. (1994). Inhibition of skin tumorigenesis by rosemary and its constituents carnosol and ursolic acid. Cancer Research 54(3):701–708.

Kerr, J. F. R., Winterford, C. M., Harmon, B. V. (1994). Apoptosis:Its significance in cancer and cancer therapy. Cancer 73: 2013–2026.

Lau, B H., Ruckle, H. C., Botolazzo, T., and Lue, P. D. (1994). Chinese medicinal herbs inhibit growth of murine renal cell carcinoma. Cancer Biotherapy 9(2):153–161.

Mohamed, A. I. and Hussein, A. S. (1994). Chemical composition of purslane (*Portulaca oleracea*). Plant Foods for Human Nutr. 45:1–9.

Parry, O., Okwuasaba, F. K., and Ejike, C. (1987). Preliminary clinical investigation into the muscle relaxant actions of an aqueous extract of *Portulaca oleracea* applied topically. J. Ethnopharm. 21:99–106.

Parry, O., Marks, J. A. and Okwuasaba, F. K. (1993). The skeletal muscle relaxant action of *Portulaca oleracea:* role of potassium ions. J. Ethnopharm. 40:187–194.

Retsas, S. (1986) On the antiquity of cancer: from Hippocrates and Galen. In: Retsas, S. ed. Palaeo-oncology: the antiquity of cancer. London: Ferrand Press, 41–53.

Simopoulos. A. P., Norman, H. A., Gillaspy, J. E., and Duke, J. A. (1992). Common purslane: a source of omega-3 fatty acids and antioxidants. J. Amer College. Nutr. 11(4):374–382.

Tulloch. A. P., (1975). Leaf wax of *Portulaca oleracea*. Lipids 9(9):664–668.

Venma, O. P., Kumar, S., and Chatterjee, S. N. (1982). Antifertility effects of common edible *Portulaca oleracea* on the reproductive organs of male albino mice. Indian U. Med. Res. 75:301–310.

Wattenberg, L. W. (1993). Inhibition of carcinogenesis by non-nutrient constituents of the diet. In: Food and cancer prevention—chemical and biological aspects, edited by Waldron, K. W., Johnson, I. T., and Fenwick, G. R., The Royal Society of Chemistry, Cambridge, U. K., pp. 12–23.

William, G. T. (1991). Programmed cell death: apoptosis and oncogenesis. Cell 65:1097–1098.

The embodiments of the invention in which an exclusive property of privilege is claimed are defined as follows:

1. A method for inhibition of tumor cell growth in a mammal comprising administering to said mammal an effective amount of an aqueous extract of *Portulaca oleracea* having tumorcidal activity.

2. The method of claim 1 wherein the tumor cells are stomach tumor cells.

3. The method of claim 1 wherein the tumor cells are human tumor cells.

4. A method for inhibition of tumor cell growth in a mammal comprising administering to said mammal an effective amount of a pharmaceutical composition comprising an aqueous extract of *Portulaca oleracea* having tumorcidal activity and a pharmaceutically acceptable carrier.

5. The method of claim 4 wherein the tumor cells are stomach tumor cells.

6. The method of claim 4 wherein the tumor cells are human tumor cells.

7. A method for the treatment of tumor cell growth in a mammal comprising administering to said mammal an effective amount of a pharmaceutical composition comprising an aqueous extract of *Portulaca oleracea* having tumorcidal activity and a pharmaceutically acceptable carrier.

8. The method of claim 7 wherein the pharmaceutical composition is administered at a range from about 0.005 mg/gm body weight to about 0.5 mg/gm body weight.

9. The method of claim 8 wherein the pharmaceutical composition is administered at a dose of about 0.007 mg/gm body weight to about 0.015 mg/gm body weight.

10. A method for the treatment of tumor cell growth in a mammal comprising administering to said mammal an effective amount of an aqueous extract of *Portulaca oleracea* having tumorcidal activity.

11. The method of claim 10 wherein the aqueous extract is administered at a range from about 0.005 mg/gm body weight to about 0.5 mg/gm body weight.

12. The method of claim 11 wherein the aqueous extract is administered at a dose of about 0.007 mg/gm body weight to about 0.015 mg/gm body weight.

* * * * *